United States Patent
Toskala et al.

(10) Patent No.: US 10,043,256 B2
(45) Date of Patent: Aug. 7, 2018

(54) MEASUREMENT OF TISSUE PAPER

(71) Applicant: VALMET AUTOMATION OY, Espoo (FI)

(72) Inventors: Marko Toskala, Orivesi (FI); Ismo Mäkelä, Tampere (FI); Markku Mäntylä, Kangasala (FI)

(73) Assignee: VALMET AUTOMATION OY, Espoo (FI)

( * ) Notice: Subject to any disclaimer, the term of this patent is extended or adjusted under 35 U.S.C. 154(b) by 145 days.

(21) Appl. No.: 14/649,037

(22) PCT Filed: Nov. 26, 2013

(86) PCT No.: PCT/FI2013/051107
§ 371 (c)(1),
(2) Date: Jun. 2, 2015

(87) PCT Pub. No.: WO2014/087046
PCT Pub. Date: Jun. 12, 2014

(65) Prior Publication Data
US 2016/0019686 A1    Jan. 21, 2016

(30) Foreign Application Priority Data
Dec. 4, 2012 (FI) .................................... 20126266

(51) Int. Cl.
*G06T 7/00* (2017.01)
*B31F 1/12* (2006.01)
(Continued)

(52) U.S. Cl.
CPC .............. *G06T 7/0004* (2013.01); *B31F 1/12* (2013.01); *D21F 7/06* (2013.01); *D21G 9/0009* (2013.01);
(Continued)

(58) Field of Classification Search
CPC ........ G06T 7/0004; B31F 1/12; D21G 9/0009
See application file for complete search history.

(56) References Cited

U.S. PATENT DOCUMENTS 3,879,257 A * 4/1975 Gentile .................. B31F 1/126
162/112
3,974,025 A * 8/1976 Ayers .................... D21F 11/006
139/383 A
(Continued)

FOREIGN PATENT DOCUMENTS

WO        99/49118 A1    9/1999
WO        01/22784 A1    3/2001
(Continued)

OTHER PUBLICATIONS www.valmet.com—"Valmet's breast roll shaker improves board and paper quality" Sep. 2015, pp. 1-3.*
(Continued)

*Primary Examiner* — Mia M Thomas
(74) *Attorney, Agent, or Firm* — Oliff PLC

(57) ABSTRACT

A topographical imaging device is placable after a creping process which causes folds to the tissue sheet and the topographical imaging device provides image data having three-dimensional information on the tissue sheet. A data processing device determines, on the basis of a shape of a cross section of at least one fold of creping of the tissue sheet, at least one of the following: thickness of the tissue sheet, softness of the tissue sheet.

22 Claims, 5 Drawing Sheets

(51) Int. Cl.
    *D21F 7/06*      (2006.01)
    *D21G 9/00*      (2006.01)
    *G01N 21/89*     (2006.01)
    *G01B 11/30*     (2006.01)
    *G01B 11/06*     (2006.01)
    *G06T 15/04*     (2011.01)
    *G06T 7/593*     (2017.01)

(52) U.S. Cl.
    CPC ........ *G01B 11/0691* (2013.01); *G01B 11/303* (2013.01); *G01N 21/89* (2013.01); *G06T 7/593* (2017.01); *G06T 15/04* (2013.01); *G06T 2207/10012* (2013.01); *G06T 2207/10028* (2013.01); *G06T 2207/30124* (2013.01)

(56) References Cited

U.S. PATENT DOCUMENTS

| | | | | |
|---|---|---|---|---|
| 4,978,861 | A * | 12/1990 | Sabater | G01B 11/303 250/559.23 |
| 5,209,973 | A * | 5/1993 | Wille | C09J 7/04 162/100 |
| 5,589,941 | A * | 12/1996 | Sabater | G01B 11/24 250/559.24 |
| 5,647,555 | A * | 7/1997 | Conrad | B65H 18/02 242/547 |
| 5,654,799 | A * | 8/1997 | Chase | G01N 21/86 356/429 |
| 5,730,839 | A * | 3/1998 | Wendt | D21H 17/07 162/111 |
| 6,207,734 | B1 * | 3/2001 | Vinson | B31F 1/12 162/111 |
| 6,308,886 | B1 * | 10/2001 | Benson | G06K 17/00 235/375 |
| 6,511,579 | B1 * | 1/2003 | Edwards | D21F 11/006 162/111 |
| 6,701,637 | B2 * | 3/2004 | Lindsay | D21F 5/004 162/206 |
| 6,808,790 | B2 * | 10/2004 | Chen | A61F 13/15203 162/109 |
| 7,399,378 | B2 * | 7/2008 | Edwards | D21F 11/006 156/183 |
| 7,494,563 | B2 * | 2/2009 | Edwards | D21F 11/006 162/109 |
| 7,545,971 | B2 * | 6/2009 | Shakespeare | G01B 11/306 382/141 |
| 7,789,995 | B2 * | 9/2010 | Super | B31F 1/126 162/111 |
| 7,794,566 | B2 * | 9/2010 | Edwards | D21F 11/006 162/111 |
| 8,080,130 | B2 * | 12/2011 | Harper | D21H 15/02 162/111 |
| 8,409,404 | B2 * | 4/2013 | Harper | B32B 29/005 162/111 |
| 8,871,060 | B2 * | 10/2014 | Klerelid | D21F 11/006 162/217 |
| 8,958,898 | B2 * | 2/2015 | Von Drasek | G01B 11/0608 162/100 |
| 9,238,889 | B2 * | 1/2016 | Paavola | D21F 7/06 |
| 2002/0005264 | A1 * | 1/2002 | McGary | B65H 23/24 162/202 |
| 2002/0088592 | A1 * | 7/2002 | Drew | A61F 13/15707 162/297 |
| 2002/0088596 | A1 * | 7/2002 | Lamb | D21F 1/0027 162/100 |
| 2003/0121628 | A1 * | 7/2003 | Mills | B31F 1/07 162/125 |
| 2003/0130599 | A1 * | 7/2003 | Restle | A61B 17/22029 601/2 |
| 2003/0135181 | A1 * | 7/2003 | Chen | A47L 13/16 604/374 |
| 2004/0099388 | A1 * | 5/2004 | Chen | B05C 1/165 162/134 |
| 2005/0069207 | A1 * | 3/2005 | Zakrzewski | B64D 45/0015 382/190 |
| 2005/0145352 | A1 * | 7/2005 | Hermans | D21F 11/14 162/112 |
| 2005/0156078 | A1 * | 7/2005 | Ragard | B65H 18/16 242/534 |
| 2005/0217814 | A1 * | 10/2005 | Super | B31F 1/126 162/111 |
| 2005/0236122 | A1 * | 10/2005 | Mullally | D21F 11/006 162/109 |
| 2005/0238682 | A1 * | 10/2005 | Anast | D21C 7/14 424/402 |
| 2006/0143671 | A1 * | 6/2006 | Ens | D21G 9/0009 725/105 |
| 2006/0237154 | A1 * | 10/2006 | Edwards | B31F 1/07 162/111 |
| 2007/0131367 | A1 * | 6/2007 | Mathews | D21F 11/006 162/117 |
| 2008/0013818 | A1 * | 1/2008 | Shakespeare | G01B 11/306 382/141 |
| 2008/0029235 | A1 * | 2/2008 | Edwards | D21F 11/006 162/111 |
| 2008/0099169 | A1 * | 5/2008 | Beuther | D21F 11/006 162/111 |
| 2009/0022391 | A1 * | 1/2009 | Huotilainen | G01N 21/8983 382/141 |
| 2009/0231572 | A1 * | 9/2009 | Emerich | B42D 25/29 356/71 |
| 2011/0146924 | A1 * | 6/2011 | Yeh | D21F 11/006 162/111 |
| 2011/0304332 | A1 * | 12/2011 | Mahfouz | A61F 2/3094 324/309 |
| 2012/0224758 | A1 * | 9/2012 | Treece | G06T 7/0012 382/131 |
| 2013/0116812 | A1 * | 5/2013 | Drasek | G01B 11/0608 700/103 |
| 2014/0096925 | A1 * | 4/2014 | Gorden | D21F 5/181 162/111 |
| 2014/0119633 | A1 * | 5/2014 | McCord | G01N 15/1463 382/133 |
| 2014/0133734 | A1 * | 5/2014 | Sze | D21G 9/0036 382/141 |
| 2014/0254885 | A1 * | 9/2014 | Sze | D21F 11/006 382/111 |
| 2015/0107791 | A1 * | 4/2015 | Paavola | D21F 7/06 162/111 |
| 2015/0129145 | A1 * | 5/2015 | Chou | D21H 27/40 162/116 |
| 2015/0176221 | A1 * | 6/2015 | Maladen | D21H 27/005 162/109 |
| 2015/0247290 | A1 * | 9/2015 | Burazin | A47K 10/16 162/123 |
| 2015/0299952 | A1 * | 10/2015 | Kalaniemi | D21G 5/00 348/88 |
| 2015/0380355 | A1 * | 12/2015 | Rogers | H01L 23/538 257/773 |
| 2016/0180522 | A1 * | 6/2016 | McCord | G01N 15/1463 348/77 |
| 2017/0089013 | A1 * | 3/2017 | Sze | D21H 27/005 |

FOREIGN PATENT DOCUMENTS

WO    2007024858  A1    3/2007
WO    2013070542  A1    5/2013

OTHER PUBLICATIONS

Feb. 20, 2014 Search Report issued in International Patent Application No. PCT/FI2013/051107.

Jun. 28, 2013 Search Report issued in Finnish Patent Application No. 20126266.

Dec. 1, 2014 Search Report issued in Finnish Patent Application No. 20126266.

Jun. 28, 2013 Office Action issued in Finnish Application No. 20126266.

(56) References Cited

OTHER PUBLICATIONS

Dec. 1, 2014 Office Action issued in Finnish Application No. 20126266.
Apr. 1, 2016 Office Action issued in Finnish Application No. 20126266.

* cited by examiner

MEASUREMENT OF TISSUE PAPER

FIELD

The invention relates to a measurement tissue paper.

BACKGROUND

Because softness is one of the most important properties for a user of tissue paper there have been a lot of attempts to determine it. At the moment softness is most reliably measured by a panel of specially trained human testers who perform a tactile perception of a sample of tissue for receiving impressions of sound of crumpling, color, smell and size of the sample etc. Thickness of the tissue paper plays a clear role in the determination of the softness, too. Because all of these and possibly also other features have effect on the decision of the testers, softness is a notoriously difficult and ill-defined subjective handfeel property which also depends on other psycho-physical impressions. Despite worthy attempts softness measurement has not successfully been automatized yet.

Hence, there is a need for an automatized measurement of softness.

SUMMARY

The following presents a simplified summary of the invention in order to provide a basic understanding of some aspects of the invention. Its purpose is to present some concepts of the invention in a simplified form as a prelude to the more detailed description that is presented later.

An aspect of the invention relates to apparatus of claim 1.

An aspect of the invention relates to apparatus of claim 18.

An aspect of the invention relates to a method of claim 19.

Although the various aspects, embodiments and features of the invention are recited independently, it should be appreciated that all combinations of the various aspects, embodiments and features of the invention are possible and within the scope of the present invention as claimed.

The present solution provides advantages. Softness of tissue paper can be determined reliably in an automatic manner.

BRIEF DESCRIPTION OF THE DRAWINGS

In the following the invention will be described in greater detail by means of exemplary embodiments with reference to the attached drawings, in which.

DESCRIPTION OF EMBODIMENTS

Exemplary embodiments of the present invention will now be described more fully hereinafter with reference to the accompanying drawings, in which some, but not necessarily all embodiments of the invention are shown. Indeed, the invention may be embodied in many different forms and should not be construed as limited to the embodiments set forth herein. Although the specification may refer to "an" embodiment in several locations, this does not necessarily mean that each such reference applies to a single embodiment. Single features of different embodiments may be combined to provide other embodiments.

Softness may mean bulk softness which may be determined by hand crumpling of the tissue paper because the bulk softness relates to the flexibility of a tissue paper. Bulk softness may thus depend on a thickness and/or grammage of the tissue paper. The type of fibers such as length, width, their ratio or the like of fiber may also have effect of bulk softness.

Softness may also mean surface softness which typically refers to the smoothness and texture of the tissue paper. The surface softness may be determined by a feeling obtained when fingertips are moved over the tissue paper's surface. The surface softness may depend on a shape of folds of creping. The shape of the folds may, in turn, depend on a type of fibers. The overall softness may be considered a combination of these two types of softnesses. Because the relationships of detailed features are complicated a simplified, reliable and handsfree measurement is desirable.

Figure 1:
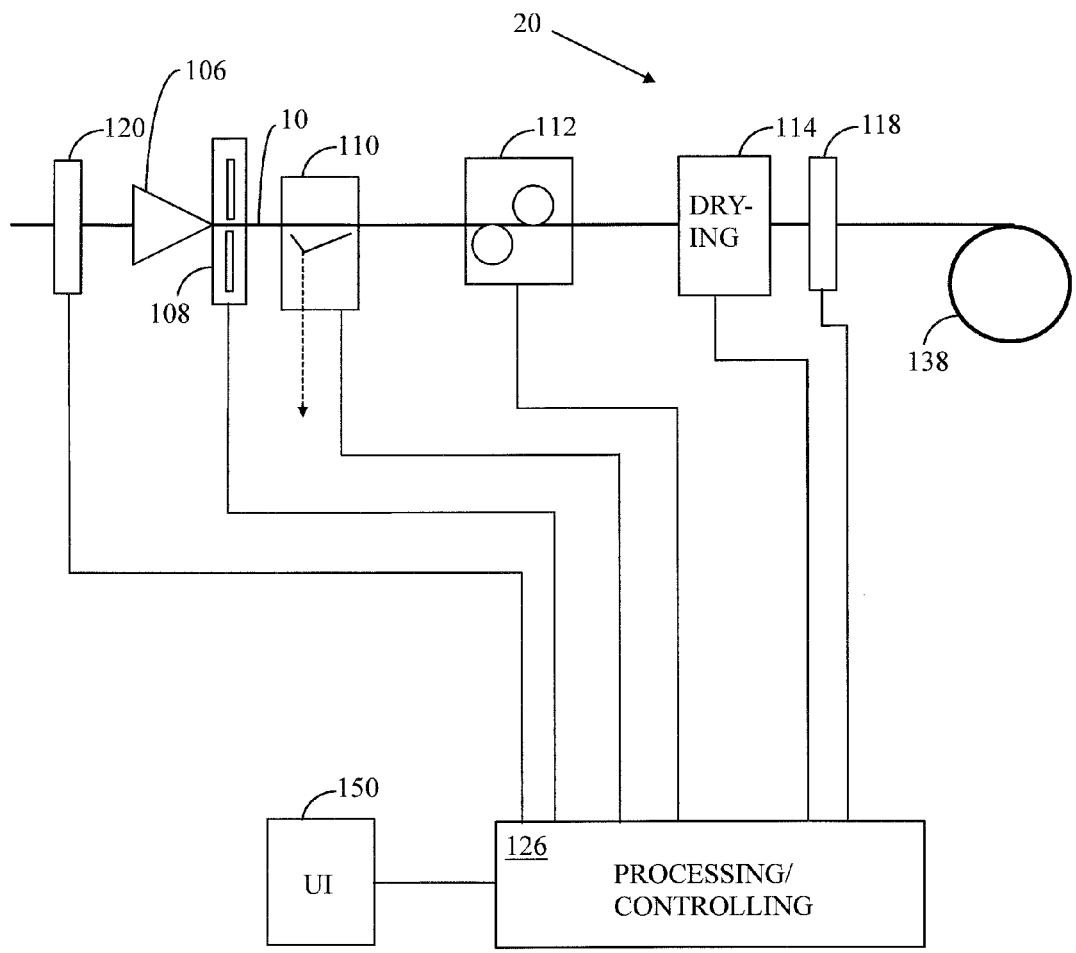
FIG. 1 shows an example of a block diagram of a paper machine.

FIG. 1 shows a principle structure of a paper machine starting from a head box 106, where pulp is fed through a slice 108 into the former 110, which may be a fourdrinier or a gap former. In the former 110, the sheet 10 is dewatered and ash, fines and fibres are removed into the short circulation. In the former 110, the pulp is fed as a sheet 10 onto the wire, and the sheet 10 is preliminarily dewatered and pressed in a press 112.

The sheet 10 is primarily dried in a dry end 20 of the paper machine where heat is introduced to the sheet for making the rest of the water to evaporate. The dry end 20 may comprise a drying section 114, cutting, and reeling, for instance. The drying section 114 also comprises a creping process. In the dry end 20, water content of the sheet is lower than 10 per cents because of preliminary drying.

There is at least one topographical imaging means 118 after the creping process, by which images of surface of the sheet 10 may be captured. There may also be at least one morphological imaging means 120, by which images of particles in the pulp may be captured.

The paper machine may be a tissue paper machine, and it may feed the tissue sheet in a reel 138 after the creping process.

In addition, it is obvious that the operation of a paper machine is known per se to a person skilled in the art, wherefore it is not described in more detail in this context.

FIG. 1 also shows a control system for the paper machine. A controller 126 may be a data processor for the image and other data. The controller 126 also represents here the control of all the processes of the paper machine including creping process and the drying process 114. The controller 126 utilizes the topographical imaging means 118 and potentially also the morphological imaging means 120 for monitoring the tissue sheet and particles in the pulp. The controller 126 may also measure the sheet 10 properties by other sensors (not shown). A user interface 150 may be coupled with the controller 126. The user interface may include a screen and a keyboard or the like.

The controller 126 may be considered as a control arrangement based on automatic data processing of the paper machine, or as a part thereof. The controller 126 may receive digital signals or convert the received analog signals to digital signals. The controller 126 may comprise at least one microprocessor and memory and process the signal according to a suitable computer program. The controller 126 may be based on a PID (Proportional-Integral-Derivative), MPC (Model Predictive Control) or GPC (General Predictive Control) control, for example.

Figure 2A:
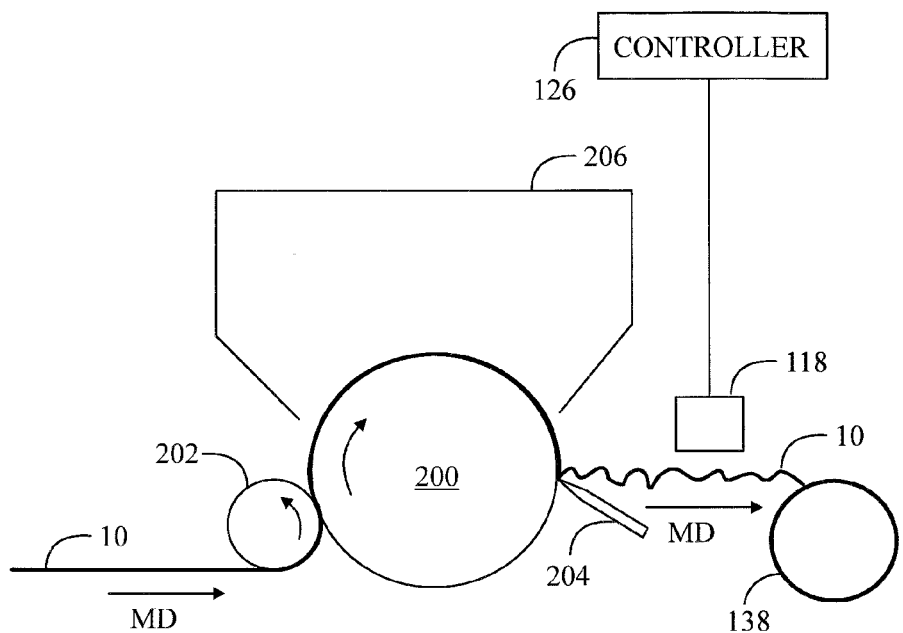
FIG. 2A shows an example of a creping process.

FIG. 2A presents a creping process in conjunction with a Yankee dryer 200. The drying and creping process may comprise an auxiliary roll 202 for pressing the sheet 10 against the Yankee roll 200, and a doctor blade 204. The Yankee drier is a heated roll which dries the sheet 10 by the heat. The Yankee roll 200 may be heated with hot steam, for example. The doctor blade 204 detaches the hot and dry sheet 10 from the surface of the Yankee roll 200 for causing the sheet 10 to become crinkled or creped. For making soft tissue paper, creping chemicals with or without softening agents may be applied to the sheet 10 before or on the Yankee roll 200. The creping chemicals, in addition to facilitating the crinkling of the paper, may lubricate the contact surfaces for reducing temperature and wear of the doctor blade 204 and the Yankee roll 200 during scraping off the sheet 10. A drier 206 is applied to blow hot air to the sheet 10 on the Yankee roll 200. After creping the topological imaging means 118 capture images of creped sheet 10. The creped sheet 10 may finally be rolled in a reel spool 138. A degree of creping Dcr depends on the size of the Yankee roll 200 and the reel spool 138 such that the degree of creping Dcr may be defined as $Dcr=100\%*(Vy-Vr)/Vy$ or $Dcr=100\%*(Vy-Vr)/Vr$, where Vy is a rotation speed of the Yankee roll 200 and Vr is a rotation speed of the reel spool 138.

Figure 2B:
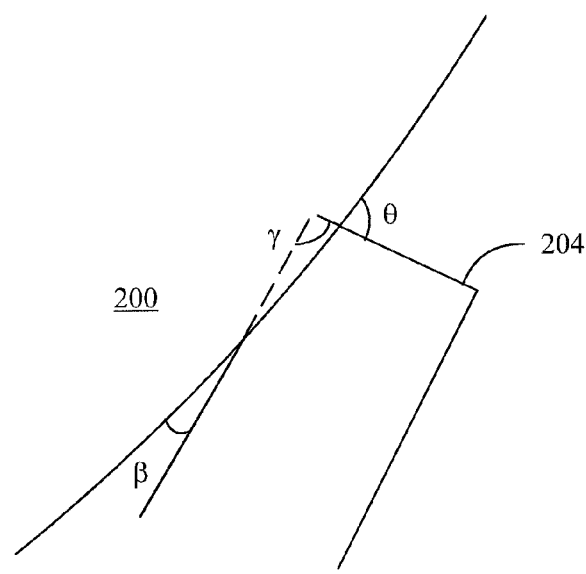
FIG. 2B shows an example of angles associated with a doctor blade.

FIG. 2B presents angles related to the doctor blade 204 and the Yankee roll 200. The angle β is an angle of contact of the doctor blade 204 with the Yankee roll 200. The angle θ is an impact angle and the angle γ is an grinding angle. By changing any of these have an effect on the creping and also on softness. For example, an increased impact angle lowers bulk and a decreased impact angle increases bulk.

Figure 3:
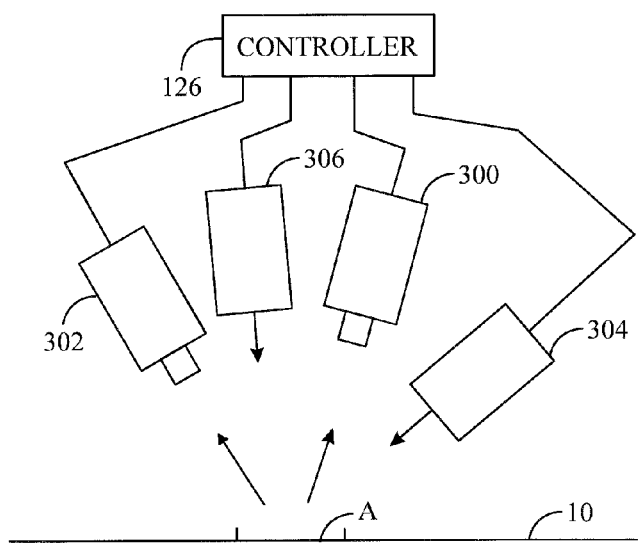
FIG. 3 shows examples of a topographical imaging arrangement.

FIG. 3 presents a measurement arrangement for capturing images from tissue sheet after creping. The area A captured by cameras 300, 302 may be from square millimeters to square centimeters, for example. The imaged area may be about 20 mm×20 mm, for example. The cameras 300, 302 may be CCD (Charge Coupled Device) or a CMOS (Complementary Metal Oxide Semiconductor) cameras. The two-dimensional images are used to form a three-dimensional representation of the tissue sheet 10. Although the three-dimensional representation mainly refers to the surface of the tissue sheet, the depth of the creping folds may be obtainable and thus one may consider that the tissue sheet may be seen and measured through.

Three-dimensional image data of the tissue sheet 10 may be obtained by photometric stereo and/or structured light methods, for example. When measuring tissue sheet, a multi-view stereo method, which may also be used to for a three-dimensional representation, can principally be considered similar to the photometric stereo method.

In the photometric stereo method, at least one camera 300, 302 captures images of the tissue sheet 10. At least two images captured from the same area of the tissue sheet have illumination of at least one illuminator 304, 306 coming from different directions. Two or more images having different illuminations may be captured at different moments of time. Two or more images having different illuminations may be captured simultaneously if different illuminations use different optical bands and the at least one camera 300, 302 has separate pixels for different optical bands. For example, two or three primary colors (red, green and blue) may be used for illuminations and a single camera 300, 302 may be designed to capture a color image with separate pixels for the primary colors. The images captured with different colors are separately computable, although captured at the same time. The photometric stereo method then creates a three-dimensional representation of the tissue sheet on the basis of the at least two two-dimensional images of the same area which are illuminated from different directions. The three-dimensional representation is based on differences in shadows and highlights in the differently illuminated images. The three-dimensional representation is computable from two-dimensional images using a suitable computer program designed for a computer vision.

The structured-light method for providing a three-dimensional representation of the tissue sheet 10 uses at least one light pattern projected by at least one illuminator 304, 306 on the tissue sheet 10. The light pattern may be a stripe pattern, for example. At least one camera 300, 302 then captures images of the at least one light pattern on the tissue sheet from a direction different from that of the projection. Because the projected pattern follows the surface shape of the tissue sheet, it becomes geometrically distorted and the distortion is visible to the at least one camera 300, 302. The three-dimensional representation is based on the comparison of the original light pattern and the distorted light pattern. The three-dimensional representation is computable from the comparison using a suitable computer program designed for computer vision.

Other methods for forming three-dimensional image information include methods based on interferometry, laser scanning and confocal microscopy which are per se known by a person skilled in the art.

Knowledge of the positions of the at least one camera 300, 302 or the at least one illuminator 304, 306 may or may not be needed in the methods for forming three-dimensional representation. The controller 126 may control the at least one camera 300, 302 and the at least one illuminator 304, 306. The controller 126 may control exposure moment and/or exposure time the at least one camera 300, 302, and duration and timing to output light from the at least one illuminator 304, 306. For measuring a moving sheet travelling 30 m/s, for instance, with a proper resolution the exposure time need to be short enough. The exposure time may be 1 µs, for example, without restricting to that. The exposure time may be caused by a flash of the at least one illuminator 304, 306 and/or by a shutter speed of the at least one camera 300, 302.

Figure 4:
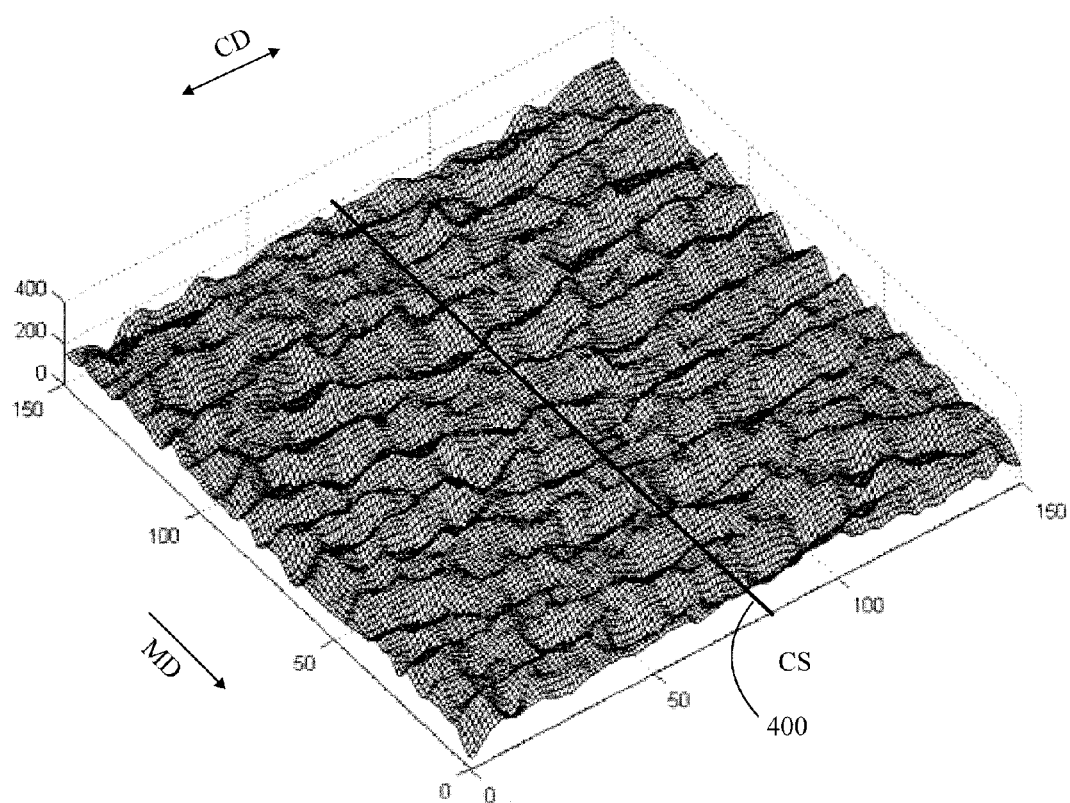
FIG. 4 shows an example of a topographical map of a soft tissue.

FIG. 4 presents an example of a topography map based on the image data having three-dimensional information on the tissue sheet 10. The scale of the axis is arbitrary. The image has been band-pass filtered. The tissue sheet 10 in FIG. 4 is soft. The softness may result from the facts that the frequency of the crepping folds of the tissue is high and the amplitude of the folds is large which makes the bulk of the tissue high. Line 400 illustrates a possible profile of a cross section (CS) of the tissue sheet 10 for measuring the folds of crepping.

Figure 5:
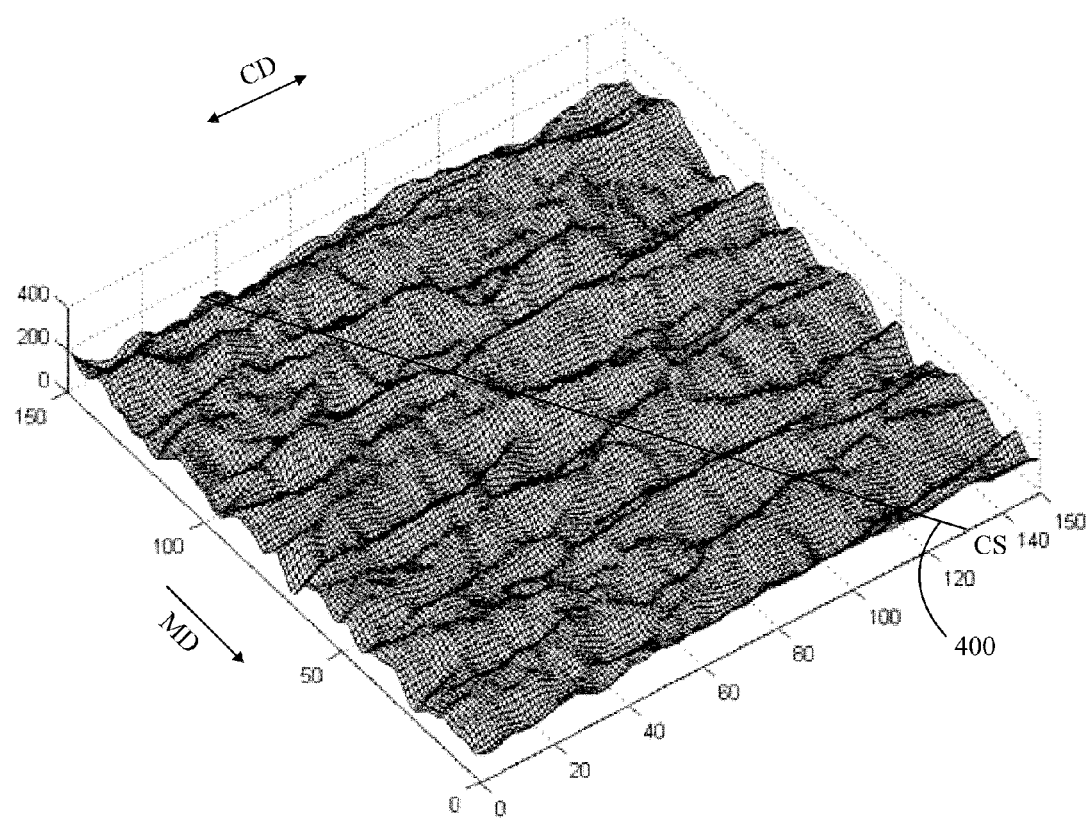
FIG. 5 shows an example of a topographical map of a tissue having low softness.

FIG. 5 presents another example of a topography map based on the image data having three-dimensional information on the tissue sheet 10. The scale of the axis is arbitrary. The softness of the tissue sheet 10 in FIG. 4 is low. The low softness may result from the facts that the frequency of the crepping folds of the tissue is low and the amplitude of the folds is small which makes the bulk of the tissue low. Line 400 illustrates a possible profile of a cross section (CS) of the tissue sheet 10 for measuring the folds of crepping.

The topographical imaging means 118 comprising the at least camera 300, 302 and the at least one illuminator 304, 306 are placed after a creping process which causes folds to the tissue sheet in the dry end of the paper machine. The topographical imaging means 118 provide image data of the tissue sheet having three-dimensional information. The image data may be presentable as topography maps such as shown in FIGS. 4 and 5. The image data may comprise at least two images captured with illumination from different directions or at least one image illuminated with the structured light. The three-dimensional information includes information on shapes of folds of creping of the tissue sheet, for example. The data processing means 126 may determine the softness of the tissue sheet 10 on the basis of the shape of a cross section of at least one fold of creping of the tissue sheet. Alternatively, the data processing means 126 may determine the thickness of the tissue sheet 10 on the basis of a shape of a cross section of at least one fold of creping of the tissue sheet. The cross section of the at least one fold may be formed as a cross section (CS) of the tissue sheet 10 where the direction of the cross section (CS) of the tissue sheet 10 is different from a cross direction (CD) associated with the fabrication process of the sheet 10 in the paper machine. The cross direction (CD) is a transverse direction with respect to a machine direction (MD) of the sheet 10. The machine direction (MD) of the sheet 10, in turn, is the direction of a movement the sheet 10 in the paper machine. The direction of the cross section (CS) may be parallel to the machine direction (MD). Different directions are shown in FIGS. 4 and 5, for example.

The image data may be low-pass, band-pass or high-pass filtered in the controller 126 or in the imaging means 118 such that dimensions of the desired shapes become available for the analysis. Typically the image may be spatially filtered such that larger variation range than that characteristic for folds is removed from the data. It is also possible to remove smaller variation than that of the folds from the data. Spatial frequencies larger than $2\pi/(1\ mm)$ and/or smaller $27\pi/(50\ \mu m)$ may be removed by filtering, for example.

In an embodiment, the topographical imaging means 118 may provide three dimensional image data from the surface of a moving tissue sheet. That is, the measurement may be an on-line measurement.

Figure 6:
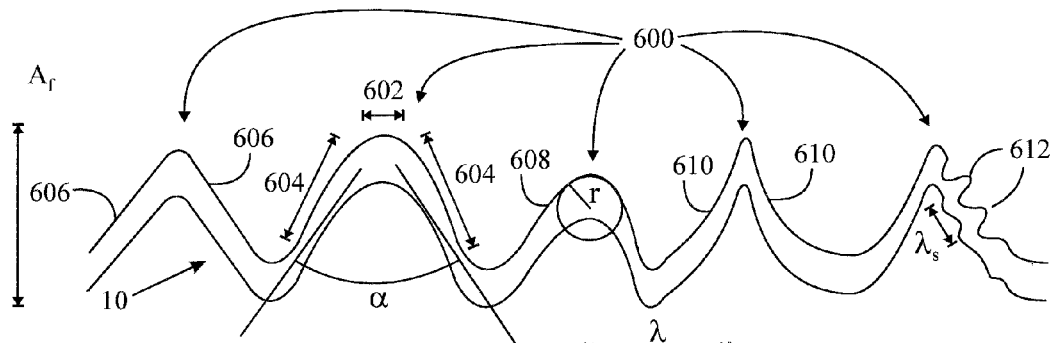
FIG. 6 shows examples of types of folds of creping.

FIG. 6 presents a general example of folds caused by the creping of the tissue sheet 10. The folds 600 of creping may have different shapes such that their size both vertically and horizontally may differ. Correspondingly, the folds 600 may have different shapes because of different fold tightness. Additionally, the distance between folds 600 may be determined as a spatial wavelength $\lambda$ of the folds 600. The spatial wavelength $\lambda$ may be from tens of micrometers to millimeters, for example.

A cross section of a fold 600 has an edge 602 and two sides 604. The sides 604 join together at the edge 602, which may be considered a kind of hinge where the sides 604 have turned to different directions. The edge 602 may have the shortest radius r of curvature for a fold 600. A distance between a crest of a fold and a trough of the fold 600 may be used to define an amplitude $A_f$ of the creping. The amplitude may be used to determine a thickness of the tissue sheet 10. In an embodiment, the maximum amplitude, the standard deviation or the like may be used to determine a thickness of the tissue sheet 10.

A fold 600 may have at least approximately straight sides 606, convex sides 608 or concave 610 sides. A fold with straight sides 606 resembles a letter V. A fold with convex sides 608 is round and bulges out whereas a fold with concave sides 610 bends inwards and is at least rather sharp at the edge. A fold 600 may be symmetrical such that the sides 604 may have the same length or a fold 600 may be asymmetrical such that the sides 604 may have different lengths. Each of the features may be used in the determination of softness.

Fold tightness may be defined as an angle $\alpha$ between sides 604 of a fold 600. A fold with convex sides 608 has typically a wider angle $\alpha$ of fold tightness than that of a fold with concave sides 610.

A fold 600 may also have subfolds 612 which are folds is a fold. Their density may be measured by determining their distance from each other as a wavelength $\lambda_s$. The wavelength of the folds 600 and subfolds 612 may be determined using a per se known Fourier analysis or the like. In addition to Fourier analysis, there are several other known methods for spectral decomposition of the image data which may provide frequency and/or wavelength information from the image data.

The folds may be analyzed on the basis of statistical quantities. In an embodiment, the analysis made in the controller 126 may be based on kurtosis Rku which measures the peakedness of the folds. Another example of the statistical analysis may be skewness Rsk. The statistical analysis may reveal the roundness or sharpness of the folds.

In an embodiment, the data processing means 126 may determine the softness of the tissue sheet on the basis of tightness of the at least one fold 600 of the creping. The tissue sheet may be found the softer the less tight the tightness of the fold 600 is, and vice versa.

In an embodiment, the data processing means 126 may determine the softness of the tissue sheet on the basis of roundness and/or sharpness of the at least one fold 600 of the creping. The rounder the at least one fold 600 is the softer the tissue sheet may be determined. The rounder the fold is the less tight it is.

In an embodiment, the controller 126 may measure the roundness and/or sharpness of the at least one fold 600 on the basis of a rate of change of the shape of each fold. The rate of change may be expressed as a slope of the curve representing the shape. The slope in turn may be formed on the basis of a derivative.

In an embodiment, tangents of the sides 604 of a fold 600 may be formed on the basis of the slope values. The tangents may be formed in a plurality of locations in the sides 604. Then the controller 126 may form a value for the angle $\alpha$ between the tangents. Typically an average angle $\alpha$ of a plurality of folds may be formed. The softness of the tissue sheet 10 may be considered to increase with the increasing angle $\alpha$ and vice versa because a wide angle refers to a rounder form.

In an embodiment, the data processing means 126 may measure a radius r of at least one fold 600 of creping. Then the data processing means 126 may determine the softness of the tissue sheet on the basis of the radius r of curvature. The image data may be low pass filtered such that an unexpectedly small radius is not used in the measurement. For example, the smallest measured radius r of curvature may be about 10 $\mu m$ for example. The larger the radius of curvature is the softer the tissue sheet may be determined.

In an embodiment, the data processing means 126 may determine the softness of the tissue sheet on the basis of a smallest radius of curvature of the at least one fold 600.

In an embodiment, the data processing means 126 may determine the softness of the tissue sheet on the basis of a number of subfolds 612 in a fold 600. The more subfolds 612 a fold 600 has the softer the tissue sheet may be felt.

In an embodiment, the data processing means 126 may determine the softness of the tissue sheet on the basis of wavelengths $\lambda_s$ of the subfolds in a fold.

In an embodiment, the data processing means 126 may determine the thickness on the basis of amplitude $A_f$ of the folds 600 of creping.

In an embodiment, the data processing means 126 may determine the thickness of the tissue sheet on the basis of maximum amplitude of the folds 600 of creping in the cross sectional direction of the tissue sheet. In general, the thicker the tissue sheet 10 is with respect to its mass, the softer the tissue sheet may be because the density of the tissue sheet is then lower. Thus, thickness of the tissue sheet may be associated with softness or it may be understood a part of softness. The mass of the tissue sheet 10 may be measured as grammage, for example, and the paper machine has typically at least one sensor for providing the controller 126 with data about the grammage. The amplitude of the folds may or may not directly be used as a measure of the thickness of the tissue sheet 10. In an embodiment, the thickness of the tissue sheet 10 may be determined as a function of the measured amplitude. The function may be predetermined on the basis of calibration measurements using sample sheets with known thickness.

In some cases the thicker the tissue sheet is, the lower the softness of the tissue sheet may be. When the tissue sheet is strongly embossed, for example, the density of the tissue sheet may actually be much higher than without embossing resulting in a tissue of a lower softness.

There are alternative or additional methods to measure the thickness of the tissue sheet 10. In an embodiment, the thickness of the tissue sheet 10 may be measured using two surface measurement sensors between which the tissue sheet 10 is or travels. Both sensors may output optical radiation to the surface of the sheet and receive a reflection from the surface. The distance to the surface may be determined using interferometry, for example. When distances between the sensors and the opposite surfaces of the tissue sheet 10 are measured, the thickness of the tissue sheet 10 may be determined on the basis of the known distance between the sensors. In an embodiment, the thickness of the tissue sheet 10 may be measured using only a sensor on one side of the tissue sheet. When the sensor outputs optical radiation, the reflections from both sides of the tissue sheet may be received by the sensor and the distance to both surfaces or the difference of the distances may be determined for measuring the thickness of the tissue sheet. The above mentioned two-sided measurement and the one-sided measurement are known per se and that is why they are not explained in more detail here.

By measuring both thickness of the tissue sheet 10 and the grammage, it is possible to form bulk of the tissue sheet 10. Furthermore, softness of the tissue sheet 10 may additionally be formed on the basis of the bulk because the bulk refers to a density of the tissue sheet 10 and softness depends on the density.

In an embodiment, the controller 126 may analyze the surface roughness of the tissue sheet 10. The controller 126 may analyze the folds 600 statistically, for instance. The roughness may be measured using per se known parameters Ra, Rz, Rq, Rsk, Rv, Rp and Rt, for example, which determine a deviation from a smooth surface. The parameter Ra measures an arithmetic average roughness of vertical amplitude deviations from a mean level. The parameter Rz is the ISO 10-point parameter and it is used to measure a difference between an average of positive peaks and an average of negative peaks. The parameter Rq is the same as $R_{RMS}$ which is a root mean squared value of the measured amplitudes of the tissue sheet 10. The parameter Rv is a measure for a maximum valley depth. The parameter Rp, in turn, is a measure for a maximum peak height. The parameter Rt is a combination of the parameters Rv and Rp expressing a maximum height of the profile. At least one of these parameters represents a general shape of the folds 600 of the tissue sheet 10.

In an embodiment, the data processing means 126 may determine the softness of the tissue sheet additionally on the basis of at least one wavelength $\lambda$ of the folds 600 of creping. The wavelengths of the folds may be determined in the controller 126 by spatial power spectrum which may be based on a Fourier analysis which is known per se. In addition to Fourier analysis, there are several other known methods for spectral decomposition of the image data which may provide frequency and/or wavelength information from the image data.

An advantage of the measurement of the softness and/or thickness is that it may be used to guarantee a uniform quality for the tissue sheet. For example, when a grade change is performed, a required quality may be kept for each grade. The quality can be kept constant by controlling that the shapes of the folds of the creping are within a predetermined range from desired shapes. If the quality departs or is on the way to depart from what is desired, the controller 126 may perform at least one control action to restore the quality and/or alarm a user of the paper machine.

Figure 7:
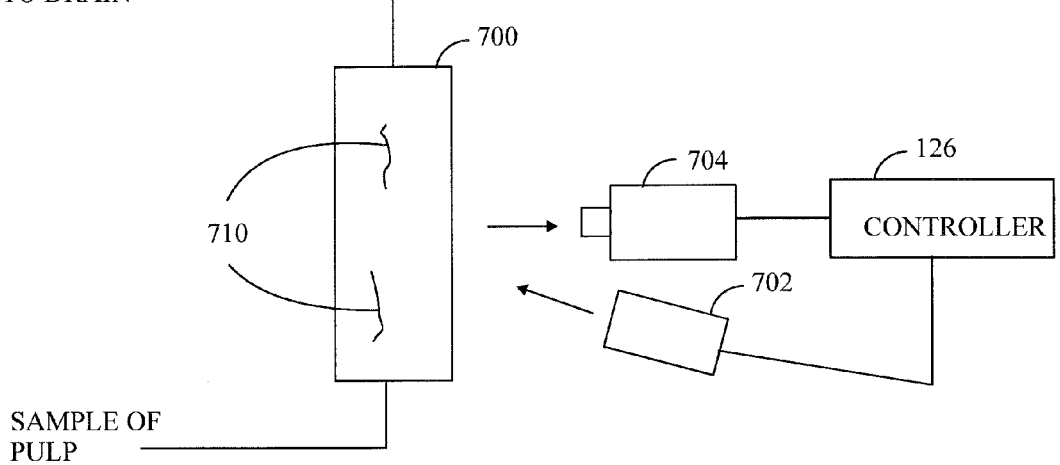
FIG. 7 shows an example of a morphological imaging arrangement.

Let us now examine the morphological imaging arrangement by means of FIG. 7. The imaging morphological arrangement comprises a measurement chamber 700, an optical power source 702 and a camera 704. The optical power source 702 may be a source emitting optical power in flashes. The optical power source 702 may be a light emitting diode, laser or a xenon lamp, for example. The camera 704, in turn, may be a CCD (Charge Coupled Device) or a CMOS (Complementary Metal Oxide Semiconductor) camera capturing images from the chamber 700 when the optical power source 702 flashes.

A cross section of one pixel of the camera 704 should correspond to a sufficiently small measure of a particle 710 such that a sharp image of the particle 710 may be captured. A cross section of a pixel may correspond to, for example, 1 µm to 10 µm without limiting to this range. The camera 704 may further comprise different optical filters for adjusting an optical bandwidth and a polarisation, but they are not necessary. The optical power source 702 may flash when a particle 710 such as a fiber is in the measurement chamber 700, in which case an image of the particle 710 may be obtained. The duration of the flash should be sufficiently short, for example 1 µs, in order to obtain an accurate image of the moving particle 710. Instead of a flashing light continuous illumination may also be used, in which case the camera 704 uses a short exposure time for capturing an image.

The measurement chamber 700 transmits the optical radiation used in the measurement and it may be equilateral or oblong in cross section. A low consistency suspension, whose consistency ranges, for example, from 0.005 to 0.001% may flow downwards in FIG. 7. Such a suspension may be obtained from the pulp fed to the paper machine by diluting the pulp. The inside measure in the direction of the normal of the inner surface may be about 0.5 mm. Fibers in the suspension may flow substantially one by one through the measurement chamber 700. The average length L of a fiber may be approximately 0.5 mm-4 mm and the thickness W may be 20-40 μm, for example, the length and thickness having influence on softness of the tissue sheet 10.

In an embodiment, the morphological imaging means 120 may measure at least one morphological feature associated with particles used in manufacturing the tissue sheet, and the data processing means 126 may additionally determine the softness on the basis of the at least one morphological feature.

In an embodiment, the morphological feature may be a length of a particle.

In an embodiment, the morphological feature may be a thickness of a particle.

In an embodiment, the morphological feature may be a thickness of a wall of a particle.

In an embodiment, the morphological feature may be a ratio of length and width of a particle.

A plurality of factors may have effect on the overall softness of tissue sheet. The overall softness may depend on the type of fibers, a level of refining, a level of wet pressing, or the use of additives, for example.

In an embodiment, the controller 126 may control the doctor blade 204 for making the desired shapes to the fold of the creping. In an embodiment, at least one of the contact, grinding and impact angles of the doctor blade 204 may be measured and controlled on the basis of the measurement of the shape of the folds of the creping and if necessary any of the angles may be changed for reaching a quality of the creping.

In an embodiment, the pressure of the doctor blade 204 against the Yankee roll 200 may be measured and controlled on the basis of the measurement of the shape of the folds of the creping and if necessary the pressure may be changed for reaching a quality of the creping.

In an embodiment, the controller 126 may measure wear of the doctor blade 204 on the basis of the measurement of the shape of the folds of the creping. The doctor blade 204 may be changed if the result of the measurement shows that the doctor blade 204 is too worn.

In an embodiment, the controller 126 may measure blockage associated with the doctor blade 204 on the basis of the measurement of the shape of the folds of the creping. If parts of sheet 10 or other material is stratified on the doctor blade 204 or between the doctor blade and the Yankee roll 200, it may cause changes in the folds of the creping which may nearly immediately be noticed by the topology measurement. Thus a quick repair may be made to the doctor blade 204 and/or the Yankee roll 200.

In an embodiment, the controller 126 may measure the vibration of the doctor blade 204 on the basis of the measurement of the shape of the folds of the creping. A vibrating doctor blade 204 may form folds of creping the shape of which is varying according to the vibration of the doctor blade 204. Thus an almost instant repair may be made to the doctor blade 204.

In an embodiment, the controller 126 may measure dosing of the chemicals in conjunction with the Yankee roll 200 on the basis of the measurement of the shape of the folds of the creping. If the dosing of the chemicals changes, it also causes changes in the shape of the folds of the creping. Thus an almost instant correction may be made to the chemical dosing.

Figure 8:
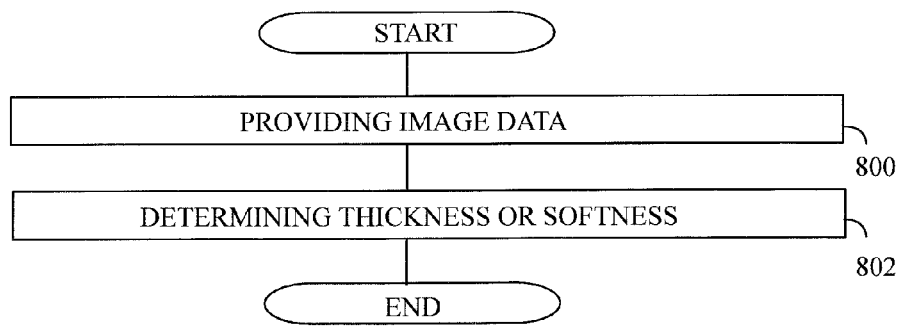
FIG. 8 presents an example of a flow chart of the method.

FIG. 8 presents an example of a flow chart of the method. In step 800, providing, by a topographical imaging means, image data having three-dimensional information on the tissue sheet having folds caused by a creping process. In step 802, a data processing means determines, on the basis of a shape of a cross section of at least one fold of creping of the tissue sheet, at least one of the following: thickness of the tissue sheet, softness of the tissue sheet.

The controller 126 may comprise a state machine such as a computer and a suitable computer program or they may be parts of the main controller 126 which may also be realized as at least one computer with at least one computer program. In an embodiment, the device implementing aspects of the invention may be realized as software, or computer program or programs in a processing system, a server or a set of computers of a web service system connected to the Internet.

The computer programs may be in source code form, object code form, or in some intermediate form, and it may be stored in some sort of carrier, which may be any entity or device capable of carrying the program. Such carriers include a record medium, computer memory, read-only memory, and software distribution package, for example. Depending on the processing power needed, the computer program may be executed in a single electronic digital controller or it may be distributed amongst a number of controllers.

It will be obvious to a person skilled in the art that, as technology advances, the inventive concept can be implemented in various ways. The invention and its embodiments are not limited to the examples described above but may vary within the scope of the claims.

What is claimed is:

1. A paper machine for creping a tissue sheet, comprising:
    a blade configured to detach the tissue sheet from a roll and cause the tissue sheet to be creped for measuring said tissue sheet, having folds caused by a creping process;
    at least one camera configured to capture at least one image of the creped tissue sheet, as the creped tissue sheet is moving from the roll to a spool, for providing image data having three-dimensional information on the creped tissue sheet; and
    a processor configured to determine thickness of the creped tissue sheet on the basis of a shape of a cross section and amplitude of at least one fold of creping of the creped tissue sheet in the image data,
    wherein the processor is further configured to generate a signal to change a parameter of the blade based on the determined thickness in order to produce a creped tissue sheet having a desired thickness.

2. The apparatus of claim 1, wherein the processor is further configured to provide three dimensional image data from the surface of a moving tissue sheet.

3. The apparatus of claim 1, wherein the processor is further configured to determine softness of the tissue sheet on the basis of tightness of the at least one fold of the creping.

4. The apparatus of claim 1, wherein the processor is further configured to determine softness of the tissue sheet on the basis of roundness and/or sharpness of the at least one fold of the creping.

5. The apparatus of claim 1, wherein the processor is further configured to determine softness of the tissue sheet on the basis of a radius of curvature of the at least one fold.

6. The apparatus of claim 1, wherein the processor is further configured to determine softness of the tissue sheet on the basis of a smallest radius of curvature of the at least one fold.

7. The apparatus of claim 1, wherein the processor is further configured to determine softness of the tissue sheet on the basis of a number of subfolds in a fold.

8. The apparatus of claim 1, wherein the processor is further configured to determine softness of the tissue sheet on the basis of wavelengths of the subfolds in a fold.

9. The apparatus of claim 1, wherein the processor is further configured to determine the thickness on the basis of amplitude of the folds of creping.

10. The apparatus of claim 1, wherein the processor is further configured to determine the thickness of the tissue sheet on the basis of at least one statistical quantity of the folds of creping.

11. The apparatus of claim 1, wherein the processor is further configured to determine softness of the tissue sheet on the basis of roughness caused by the at least one fold of creping.

12. The apparatus of claim 1, wherein the processor is further configured to determine softness of the tissue sheet additionally on the basis of at least one wavelength of the folds of creping.

13. The apparatus of claim 1, wherein the processor is further configured to:
measure at least one morphological feature associated with particles used in manufacturing the tissue sheet, and
determine softness of the tissue sheet on the basis of the at least one morphological feature.

14. The apparatus of claim 13, wherein the morphological feature is a length of a particle.

15. The apparatus of claim 13, wherein the morphological feature is a thickness of a particle.

16. The apparatus of claim 13, wherein the morphological feature is a thickness of a wall of a particle.

17. The apparatus of claim 13, wherein the morphological feature may be a ratio of length and width of a particle.

18. A data processing apparatus, comprising:
at least one processor;
a blade configured to detach a tissue sheet from a roll and cause the tissue sheet to be creped for measuring said tissue sheet, having folds, caused by a creping process; and
at least one memory including a computer program code, wherein the at least one memory, with the at least one processor and the computer program code, is configured to cause the at least one processor to:
obtain, from at least one camera for capturing at least one image for providing image data having three-dimensional information, the image data having three-dimensional information on a creped tissue sheet as the creped tissue sheet is moving from a roll to a spool, the creped tissue sheet having folds caused by the creping process, wherein the creped tissue sheet is caused to be creped when detached from the roll by the blade; and
determine thickness of the creped tissue sheet on the basis of a shape of a cross section and amplitude of at least one fold of creping of the creped tissue sheet in the image data, and
wherein the processor is further configured to generate a signal to change a parameter of the blade based on the determined thickness in order to produce a creped tissue sheet having a desired thickness.

19. The data processing apparatus of claim 18, wherein the at least one memory, with the at least one processor and the computer program code, is configured to cause the at least one processor to determine softness of the tissue sheet on the basis of a smallest radius of curvature of the at least one fold.

20. A method for measuring tissue sheet, the method comprising:
detaching a tissue sheet from a roll with a blade configured to cause the tissue sheet to be creped for measuring folds caused by a creping process;
capturing, by at least one camera, at least one image of the creped tissue sheet, as the creped tissue sheet is moving from the roll to a spool, for providing image data having three-dimensional information on the creped tissue sheet; and
determining, by a processor, thickness of the creped tissue sheet on the basis of a shape of a cross section and amplitude of at least one fold of creping of the creped tissue sheet in the image data,
wherein the processor is further configured to generate a signal to change a parameter of the blade based on the determined thickness in order to produce a creped tissue sheet having a desired thickness.

21. The method for measuring tissue sheet of claim 20, wherein the determining step determines softness of the tissue sheet on the basis of a smallest radius of curvature of the at least one fold.

22. An apparatus, comprising:
a blade configured to detach the tissue sheet from a roll and cause the tissue sheet to be creped;
at least one camera; and
a processor for measuring a moving tissue sheet having folds caused by a creping process, wherein
the at least one camera is configured to capture at least one image of the creped tissue sheet, as the creped tissue sheet is moving from the roll to a spool, for providing image data having three-dimensional information on the creped tissue sheet,
the processor is further configured to determine thickness of the creped tissue sheet on the basis of a shape of a cross section and amplitude of at least one fold of creping of the creped tissue sheet in the image data, and
the processor is further configured to generate a signal to (i) change a parameter of the blade based on the determined thickness in order to produce a creped tissue sheet having a desired thickness.

* * * * *